US010023844B2

(12) United States Patent
Okada et al.

(10) Patent No.: US 10,023,844 B2
(45) Date of Patent: Jul. 17, 2018

(54) PURIFICATION METHOD OF VIRUS-LIKE PARTICLES

(71) Applicants: UMN PHARMA INC., Akita-shi, Akita (JP); Timo Vesikari, Tampere (FI); Vesna Blazevic, Tampere (FI)

(72) Inventors: Masahiro Okada, Yokohama (JP); Akiko Mukai, Yokohama (JP); Tomonori Nishino, Yokohama (JP); Daisuke Arinobu, Yokohama (JP); Hiroyuki Ito, Yokohama (JP); Mamoru Satoh, Yokohama (JP)

(73) Assignees: UMN PHARMA INC., Akita-shi, Akita (JP); Timo Vesikari, Tampere (FI); Vesna Blazevic, Tampere (FI)

( * ) Notice: Subject to any disclaimer, the term of this patent is extended or adjusted under 35 U.S.C. 154(b) by 142 days.

(21) Appl. No.: 14/904,364

(22) PCT Filed: May 21, 2014

(86) PCT No.: PCT/JP2014/063423

§ 371 (c)(1),
(2) Date: Mar. 7, 2016

(87) PCT Pub. No.: WO2015/004996

PCT Pub. Date: Jan. 15, 2015

(65) Prior Publication Data

US 2016/0168543 A1 Jun. 16, 2016

(30) Foreign Application Priority Data

Jul. 12, 2013 (JP) ................................ 2013-146240

(51) Int. Cl.
*C12N 7/02* (2006.01)
*C12N 7/00* (2006.01)

(52) U.S. Cl.
CPC ...... *C12N 7/00* (2013.01); *C12N 2770/16023* (2013.01); *C12N 2770/16051* (2013.01)

(58) Field of Classification Search
CPC ........... C12N 2770/16023; C12N 2770/16051; C07K 14/005
See application file for complete search history.

(56) References Cited

U.S. PATENT DOCUMENTS

| | | | | |
|---|---|---|---|---|
| 6,020,182 | A | 2/2000 | Cates et al. | |
| 6,602,697 | B1 | 8/2003 | Cook, III | |
| 8,481,693 | B2 * | 7/2013 | Vedvick .................. | C12N 7/00 424/216.1 |
| 9,359,410 | B2 * | 6/2016 | Vedvick .................. | C12N 7/00 |
| 2005/0107594 | A1 | 5/2005 | Sun et al. | |
| 2010/0150961 | A1 * | 6/2010 | Vedvick .................. | C12N 7/00 424/216.1 |
| 2013/0344107 | A1 | 12/2013 | Vedvick et al. | |

FOREIGN PATENT DOCUMENTS

| | | | |
|---|---|---|---|
| JP | 2000-501418 | A | 2/2000 |
| JP | 2003-250188 | A | 7/2003 |
| JP | 2007-532477 | A | 7/2003 |
| JP | 2010-530734 | A | 9/2010 |

OTHER PUBLICATIONS

GIBCO BRL products & Reference Guide published for 2000-2001, p. 2-8.*
International Preliminary Report on Patentability and English translation of the Written Opinion of the International Searching Authority (Forms PCT/IB/338, PCT/IB/373 and PCT/ISA/237), dated Jan. 21, 2016, for International Application No. PCT/JP2014/063423.
International Search Report, issued in PCT/JP2014/063423, dated Aug. 19, 2014.
Tsutomu Kawasaki, "Hydroxyapatite as a liquid chromatographic packing", Journal of Chromatography, 1991, vol. 544, pp. 147-184.
Yae Kurosawa et al., "Development of a purification method for Japanese encephalitis virus particles using ceramic hydroxyapatite chromatography", Medicine and Biology, 2012, vol. 156, No. 6, pp. 410-416.

* cited by examiner

*Primary Examiner* — Bao Q Li
(74) *Attorney, Agent, or Firm* — Birch, Stewart, Kolasch & Birch, LLP

(57) ABSTRACT

The present invention aims at establishing a novel means for purifying norovirus VLPs. There is provided a purification method of norovirus virus-like particles, comprising: contacting solution containing norovirus virus-like particles with support for hydroxyapatite chromatography, binding the virus-like particles to the support, subsequently washing the support with buffer, and then eluting the virus-like particles from the support with buffer containing phosphate, wherein the phosphate concentration of the buffer used for elution is less than 10 mM.

7 Claims, 1 Drawing Sheet

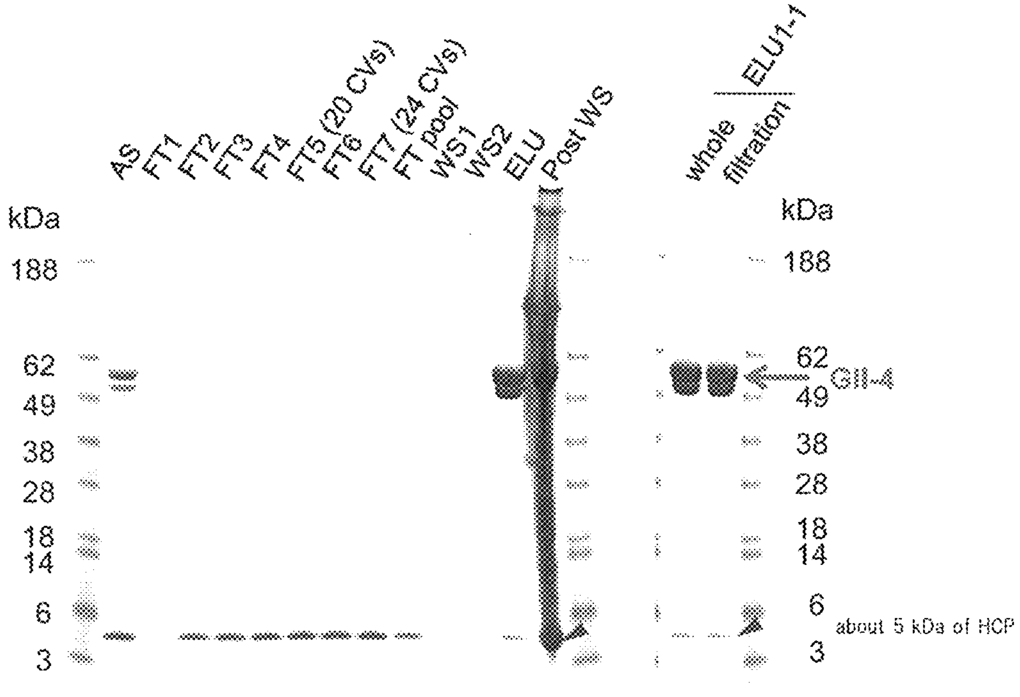
AS
FT1
FT2
FT3
FT4
FT5 (20 CVs)
FT6
FT7 (24 CVs)
FT pool
WS1
WS2
ELU
Post WS
ELU1-1
whole
filtration
kDa
188
62
49
38
28
18
14
6
3
GII-4
about 5 kDa of HCP

SEQUENCE LISTING

```
<160> NUMBER OF SEQ ID NOS: 1

<210> SEQ ID NO 1
<211> LENGTH: 539
<212> TYPE: PRT
<213> ORGANISM: Norwalk virus

<400> SEQUENCE: 1

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175
```

-continued

```
Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser His Asp Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Leu Leu Thr Gln
                325                 330                 335

Thr Thr Arg Glu Asp Gly Ser Thr Arg Ala His Lys Ala Thr Val Ser
            340                 345                 350

Thr Gly Ser Val His Phe Thr Pro Lys Leu Gly Ser Val Gln Tyr Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asn Asn His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Gln His Phe Tyr Gln Glu Ala
    450                 455                 460

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Val
                485                 490                 495

Thr Val Ala His Thr Gly Pro His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Ala Gly Arg Arg Arg Ala Leu
    530                 535
```

PURIFICATION METHOD OF VIRUS-LIKE PARTICLES

TECHNICAL FIELD

The present invention relates to a purification method of norovirus virus-like particles. More specifically, the present invention relates a purification method of norovirus virus-like particles using phosphate buffer at low concentration by hydroxyapatite chromatography.

BACKGROUND ART

Norovirus is a virus that causes acute gastroenteritis such as vomiting and diarrhoea. Norovirus causes food poisoning from eating oysters and the like, and orally infects humans via feces or vomited material.

It is known that particles called as virus-like particles (VLPs) that resemble viral particles are formed when a baculovirus vector incorporated with the structural protein coding region of norovirus genome is expressed in insect cells. Though VLPs resemble viral particles in appearance, they do not contain virus genome and is not infectious.

Norovirus vaccine has been recently developed using VLPs as antigens and patent applications concerning it have been filed (Japanese Translation of PCT International Application Publication Nos. JP-T-2010-505766 and JP-T-2011-530295). In order to produce such norovirus vaccine, it is necessary to purify VLPs from the culture. As a purification method of VLPs of norovirus, there has been known a method disclosed in Patent Literature 1.

In Patent Literature 1, a method of purifying VLPs of norovirus using a multistep chromatographic process is disclosed (for example, claim 1), and as one example of the chromatography, chromatography using hydroxyapatite is listed (for example, claim 37). Further, Patent Literature 1 discloses that buffer containing phosphate at such high concentration as 10-1000 mM is used (for example, claim 59). In particular, it discloses that buffer containing phosphate at such high concentration as 100-200 mM is required to selectively elute VLPs from a hydroxyapatite support (for example, paragraph [0107]).

CITATION LIST

Patent Literature

Patent Literature 1: Japanese Translation of PCT International Application Publication No. JP-T-2010-530734

SUMMARY OF INVENTION

Technical Problem

In order to produce norovirus vaccine using VLPs as antigens, high-purity VLPs are required. In these technical situations, the object of the present invention is to provide a novel means for purifying norovirus VLPs.

Solution to Problem

The present inventors have found that contaminating proteins are also eluted when VLPs are eluted with a high concentration phosphate buffer, such as the buffer described in Patent Literature 1 and that such a problem can be solved by using much lower concentration phosphate buffer than the buffer described in Patent Literature 1. Thus, the present invention has been achieved.

Specifically, the present invention provides the following (1) to (7).

(1) A purification method of norovirus virus-like particles, comprising: contacting solution containing norovirus virus-like particles with support for hydroxyapatite chromatography, binding the virus-like particles to the support, subsequently washing the support with buffer, and then eluting the virus-like particles from the support with buffer containing phosphate, wherein the phosphate concentration of the buffer used for elution is less than 10 mM.

(2) The purification method of norovirus virus-like particles according to (1), wherein the phosphate concentration of the buffer used for elution is 3 to 7 mM.

(3) The purification method of norovirus virus-like particles according to (1) or (2), wherein the buffer used for washing is buffer containing phosphate whose concentration is less than 10 mM.

(4) The purification method of norovirus virus-like particles according to (3), wherein the phosphate concentration of the buffer used for washing is 3 to 7 mM.

(5) The purification method of norovirus virus-like particles according to any one of (1) to (4), wherein the solution containing norovirus virus-like particles is culture supernatant of microorganisms or cells expressing a nucleic acid sequence of norovirus.

(6) The purification method of norovirus virus-like particles according to any one of (1) to (4), wherein the solution containing norovirus virus-like particles is culture supernatant of insect cells expressing a nucleic acid sequence of norovirus.

(7) The purification method of norovirus virus-like particles according to (5) or (6), wherein the nucleic acid sequence of norovirus is a nucleic acid sequence encoding norovirus structural protein VP1.

This specification includes the contents as disclosed in the specification and/or drawings of Japanese Patent Application (Patent Application No. 2013-146240), which is a priority document of the present application.

Advantageous Effects of Invention

Since the purification method of the present invention enables obtaining highly pure norovirus VPLs, it becomes possible to efficiently produce norovirus vaccine using VLPs as antigens.

BRIEF DESCRIPTION OF DRAWING

FIG. 1 is a photograph showing the results of electrophoresis of sample of each purification step.

DESCRIPTION OF EMBODIMENTS

Hereinafter, the present invention will be described in detail.

The purification method of norovirus virus-like particles of the present invention comprising: contacting solution containing norovirus virus-like particles with support for hydroxyapatite chromatography, binding the virus-like particles to the support, subsequently washing the support with buffer, and then eluting the virus-like particles from the support with buffer containing phosphate, wherein the phosphate concentration of the buffer used for elution is less than 10 mM.

Norovirus in the present invention means a virus that belongs to the family Caliciviridae and the genus Norovirus. Norwalk virus is the only species of the genus Norovirus at present. However, if a new virus belonging to this genus is found in the future, it is included in "Norovirus" in the present invention.

A virus-like particle in the present invention means a hollow particle that has only viral outer shell without viral genome inside the shell.

The phosphate concentration of the buffer used for elution (the elution buffer) may be less than 10 mM, but is preferably 3 to 7 mM, more preferably 4 to 6 mM. The elution buffer may contain substances other than phosphate, such as sodium chloride, ammonium sulfate. If it contains sodium chloride, the concentration is preferably 100 to 200 mM, more preferably 120 to 180 mM, and particularly preferably 140 to 160 mM. The pH of the elution buffer is preferably 7.0 to 8.0 mM, more preferably 7.2 to 7.8, and particularly preferably 7.4 to 7.6.

Except for the above elution buffer, the purification method of the present invention can be performed according to the known method (for example, the method described in Japanese Translation of PCT International Application Publication No. JP-T-2010-530734).

As the solution containing norovirus virus-like particles, for example, culture supernatant of microorganisms or cells expressing a nucleic acid sequence of norovirus can be used. Such culture supernatant can be prepared, for example, as follows. First, the nucleic acid sequence encoding VP1 of norovirus is incorporated into a commercially available vector. This recombinant vector is introduced into hosts (cells or microorganisms), and the nucleic acid sequence is expressed. Then, host cells and the like are cultivated for a certain period of time. The cells are disrupted if necessary, and by methods such as centrifugal separation of the obtained culture, the culture supernatant can be obtained.

As nucleic acid sequences of norovirus, a nucleic acid sequence encoding norovirus VP2 in addition to a nucleic acid sequence encoding norovirus VP1 may be expressed. The amino acid sequence of VP1 or VP2 of each norovirus strain and the nucleic acid sequence encoding it are published in such a database as GenBank. For example, registered numbers of the sequences of norovirus include M87661 of Norwalk virus, L07418 of Southampton virus, U04469 of Desert Shield virus, AB042808 of Chiba virus, U07611 of Hawaii virus, U70059 of Snow Mountain virus, AY032605 of Maryland virus, AB031013 of Seto virus, AF145896 of Camberwell, X86557 of Lordsdale virus, AJ004864 of Grimsby virus, U22498 of Mexico virus, AY502023 of Houston virus, and AY652979 of Parris Island.

The vector and the hosts (cells or microorganisms) into which it is introduced are not limited, but baculovirus vector and insect cell are preferably used. As the baculovirus vector, for example, pFastBac vector (Invitrogen), BD BaculoGold (BD Biosciences), and the like can be used. As the insect cell, for example, Sf9 cell, HighFive cell, and the like can be used.

Cultivation period of insect cells transfected with baculovirus vector is usually about 3 days (for example, International Publication WO96/37624). However, in the present invention, the cultivation preferably continues until the viability of the insect cells reaches 10% or less (for example, the cultivation continuing for 5 days or more). By cultivating cells until the cell viability is low, the contents of cells are released to the culture solution by death of the cells. This provides a benefit of eliminating the need for the process for disrupting the cells. Further, there is an advantage that the purity of the protein derived from norovirus is increased because protease released by death of the cells decomposes proteins derived from the insect cells.

The support for hydroxyapatite chromatography to be used is not specifically limited, and commercially available support, for example, Ceramic Hydroxyapatite Type I Support (Bio-Rad), Ceramic Hydroxyapatite Type II Support (Bio-Rad), or Fluoroapatite support (Bio-Rad) can be used.

Contact of the solution containing norovirus virus-like particles with the support may be performed by passing the solution containing norovirus virus-like particles through the column filled with the support.

Washing the support can be performed according to a known method. For example, it can be performed by passing about 4 to 8 CVs (column volumes) of buffer through the column filled with the support at a flow rate of about 100 to 200 mL/min. Washing may be performed more than once by using two or more kinds of buffer.

The buffer used for washing (the washing buffer) is not limited as long as it can eliminate impurities without eluting the virus-like particles. For example, MES buffer and the like may be used, but buffer containing phosphate whose concentration is less than 10 mM is preferably used, as is the case with the elution buffer.

The phosphate concentration of the washing buffer may be less than 10 mM, but is preferably 3 to 7 mM, more preferably 4 to 6 mM. The washing buffer may contain substances other than phosphate, such as sodium chloride, ammonium sulfate. If it contains sodium chloride, the concentration is preferably 1 to 100 mM, more preferably 20 to 80 mM, and particularly preferably 40 to 60 mM. If washing is performed twice, washing with buffer that does not contain sodium chloride is preferably performed before washing with buffer that contains sodium chloride. The pH of the washing buffer is preferably 6.0 to 7.0 mM, more preferably 6.2 to 7.2, and particularly preferably 6.4 to 6.6.

If elution fraction obtained by the above purification method is subjected to purification, such as hydrophobic interaction chromatography, anion exchange chromatography, or ultrafiltration, higher-purity VLPs can be obtained.

Examples

The present invention will be explained more specifically with reference to the following Examples. However, the present invention is not limited thereto.

(1) Experimental Methods

1 Devices and Reagents

Devices, reagents, and the like used in the Example are shown in the table below.

TABLE 1

| Material | Grade | Vender |
|---|---|---|
| AKTApilot | — | GE healtheare |
| Geramic Hydroxyapatite (GHT) Type I #157-0040 | GMP | BioRad or equivalent |
| Filter, 0.45 + 0.8 μm (or 0.45 + 0.2 μm) Sartopore 2#5445306G8 Acropak 1000 Supor Membrane #PN12994 | GMP | Sartorius Pall, or equivalent |
| NaCl (MW 58.44) #31320-34 | G.R. | Nacalai tesque or equivalent |
| $Na_2HPO_4$•$12H_2O$ (MW 358.14) #31723-64, #31723-35 | G.R. | Nacalai tesque or equivalent |

TABLE 1-continued

| Material | Grade | Vender |
|---|---|---|
| $NaH_2PO_4$•$2H_2O$ (MW 156.01) #31718-15 | G.R. | Nacalai tesque or equivalent |
| NaOH (MW 40.0) #31511-05 | G.R. | Nacalai tesque or equivalent |

2 Buffers 2.1 CHT Equilibration Buffer (CHT EQW); 5 mM Phosphate Buffer, pH6.5

$NaH_2PO_4.2H_2O$ (3.12 g), $Na_2HPO_4.12H_2O$ (1.90 g), and MilliQ (registered trademark) (5.0 kg) were mixed at room temperature for 5 minutes. The pH of the buffer was measured to be pH6.5 and stored at 2 to 8° C.

2.2 CHT Wash Buffer (CHT WS); 50 mM NaCl, 5 mM Phosphate Buffer, pH6.5

$NaH_2PO_4.2H_2O$ (2.73 g), $Na_2HPO_4.12H_2O$ (2.69 g), NaCl (14.61 g), and MilliQ (registered trademark) (4.9 kg) were mixed at room temperature for 5 minutes. The pH of the buffer was measured to be pH6.5 and stored at 2 to 8° c.

2.3 CHT Elution Buffer (CHT ELU); 150 mM NaCl, 5 mM Phosphate Buffer, pH7.5

$NaH_2PO_4.2H_2O$ (0.59 g), $Na_2HPO_4.12H_2O$ (7.62 g), NaCl (43.8 g), and MilliQ (registered trademark) (4.9 kg) were mixed at room temperature for 5 minutes. The pH of the buffer was measured to be pH7.5 and stored at 2 to 8° C.

2.4 CHT Postwash buffer (CHT POST WS); 250 mM NaCl, 200 mM phosphate buffer, pH6.7

$NaH_2PO_4.2H_2O$ (24.96 g), $Na_2HPO_4.12H_2O$ (85.95 g), NaCl (29.2 g), and MilliQ (registered trademark) (2 kg) were mixed at room temperature for 5 minutes. The pH of the buffer was measured to be pH6.7 and stored at 2 to 8° C.

2.5 CHT Regeneration Buffer 1 (CHT REG1); 500 mM Sodium Phosphate Buffer at Neutral pH $NaH_2PO_4.2H_2O$ (156 g), $Na_2HPO_4.12H_2O$ (537.5 g), and MilliQ (registered trademark) (4.3 kg) were mixed at room temperature for 5 minutes. The pH of the buffer was measured to be neutral pH (for example, pH6.7) and stored at room temperature.

2.6 CHT Regeneration Buffer 2 (CHT REG2); 1M NaCl, 6 M Urea Containing 5 mM Phosphate at Neutral pH Urea (1802 g), $NaH_2PO_4.2H_2O$ (3.9 g), $Na_2HPO_4.12H_2O$ (8.95 g), NaCl (292.5 g), and MilliQ (registered trademark) (2.9 kg) were mixed at room temperature for 5 minutes. The pH of the buffer was measured to be neutral pH (for example, pH7.0) and stored at room temperature.

2.7 1N NaOH Solution

NaOH (400 g) and MilliQ (registered trademark) (9.8 kg) were mixed at room temperature for 5 minutes and stored at room temperature.

2.8 0.1 N NaOH Solution

NaOH (40 g) and MilliQ (registered trademark) (10.0 kg) were mixed at room temperature for 5 minutes and stored at room temperature.

3. Procedure 3.1 Preparation of Recombinant Baculovirus

A cDNA encoding VP1, whose amino acid sequence is shown in SEQ ID NO.: 1, of a norovirus strain classified as GII-4, which was collected from an inpatient in University of Tampere, was incorporated into a transfer plasmid (pFastBac, Invitrogen). Then, the transfer plasmid incorporated with the cDNA was introduced into DH10Bac (Invitrogen), which is an *Escherichia coli* having a baculovirus genome, and the cDNA encoding the norovirus VP1 was incorporated into the baculovirus genome DNA by homologous recombination. The baculovirus genome DNA was extracted from the *Escherichia coli*, purified, and introduced into insect cells (expresSF+cells, Protein Sciences). The insect cells were cultivated, and from the culture supernatant, recombinant baculovirus was obtained.

3.2 Cultivation to Express the GII-4 VP1

The recombinant baculovirus (MOI=1) was added to the insect cells (expresSF+cells) ($1\times10^6$/mL). Then, the cells were cultivated for 5 to 6 days until the viability reached 10% or less.

3.3 Harvest and Purification

The culture solution containing the expressed GII-4 VP1 (Lot. F1274) was applied to sequential centrifugal separator (MN1, KOKUSAN) at 5,000×g and about 4 mL/sec, and the supernatant was collected. The turbidity of the supernatant was about 80 NTU. The supernatant was applied to filtration at flow late about 200 mL/min and then introduced to CHT column.

3.4 Column Preparation

CHT Type I resin 700 mL (1 mL (bed volume)=0.6 g (dry weight)) was packed in column BPG100/500 (GE) (010 cm×bed height 8.9 cm) using 0.1 N NaOH solution, and stored in 0.1 N NaOH solution.

3.5 Column Chromatography 3.5.1 Prewash

3 CVs of MilliQ (registered trademark) was loaded on the column at a flow rate of 150 cm/h (196 mL/min).

3.5.2 Equilibration

5 CVs of Equilibration buffer (CHT EQW; 5 mM phosphate buffer (pH 6.5)) was loaded on the column at a flow rate of 150 cm/h (196 mL/min).

3.5.3 Sample Loading

About 14 L of filtrated culture supernatant was loaded onto equilibrated CHT column at a flow rate of 115 cm/h (150 mL/min).

3.5.4 Wash 1

The column was washed with 6 CVs of Equilibration buffer (CHT EQW; 5 mM phosphate buffer (pH 6.5)) at a flow rate of 160 cm/h (122 mL/min).

3.5.5 Wash 2

The column was washed with 6 CVs of wash buffer (CHT WS; 50 mM NaCl, 5 mM phosphate buffer (pH6.5)) at a flow rate of 130 cm/h (170 mL/min).

3.5.6 Elution

GII-4 VP1 was eluted from the column with Elution buffer (CHT ELU; 150 mM NaCl, 5 mM phosphate buffer (pH7.5)) at a flow rate of 115 cm/h (150 mL/min).

3.5.7 Postwash

The column was washed with 6 CVs of Postwash buffer (CHT POST WS; 250 mM NaCl, 200 mM phosphate buffer, (pH6.7)) at a flow rate of 115 cm/h (150 mL/min).

3.5.8 Regeneration 1

The column was washed with 6 CVs of Regeneration buffer 1 (CHT REG1; 500 mM sodium phosphate buffer) at a flow rate of 115 cm/h (150 mL/min).

3.5.9 Regeneration 2

The column was washed with 3 CVs of Regeneration buffer 2 (CHT REG2; 1M NaCl, 6 M urea containing 5 mM phosphate buffer) at a flow rate of 115 cm/h (150 mL/min).

3.5.10 Sanitize

The column was sanitized with 1 N NaOH solution for 1 hour. 2 CVs of 1 N NaOH solution were applied to column at a flow rate of 115 cm/h (150 mL/min), and then 1 CV of 1 N NaOH solution was applied at a flow rate of 31 cm/h (40 mL/min).

3.5.11 Store

The column was washed with 3 CVs of 0.1 N NaOH solution at a flow rate of 115 cm/h (150 mL/min), and then stored.

3.6 Filter Filtration

The elution fraction was filtrated with a filter whose pore size is 0.45 μm and 0.2 μm (Sartopore 2 150, Sartorius).

3.7 Electrophoresis

80 μL of each sample was mixed with 20 μL of 5×DB (300 mmol/L Tris-HCl, pH6.8, 50% glycerol, 10% SDS, 0.5% Bromo Phenol Blue, 500 mmol/L DTT) and heated at 95° C. for 5 minutes. Then, 10 μL of each sample was applied on each lane of SDS-PAGE gel and electrophoresed at 200 V for 35 minutes. The electrophoresed gel was soaked in fixing solution (25% methanol, 10% acetic acid, 10% trichloroacetic acid (TCA)) and shaken for 5 minutes. Then, it was stained by soaking in CBB stain solution (0.1% CBB, 7.7 mmol/L ethanol, 1.75 mmol/L acetic acid) and shaking for 1 hour, and destained with destaining solution (10% acetic acid) overnight. The gel image was obtained by using a scanner. SeeBlue prestained standard (Invitrogen) was used as a molecular weight marker.

(2) Experimental Results

The results of electrophoresis of sample of each purification step are shown in FIG. 1. The letters above each lane represent the following: "AS (Applied Sample)" represents an unpurified sample to be loaded on the column; "FT (Flow Through)" represents a sample passed through the column; "FT1" to "FT7" represent a small amount of samples that were collected per about 4 CVs when 24 times amount of column volume (24 CVs) of AS was loaded; "FT pool" represents a pool gathered from all amount of FT; "WS1 (Wash 1)" and "WS2 (Wash 2)" represent samples collected from the elute from the column in Wash 1 and Wash 2, respectively; ELU (Elution) represents a fraction containing the GII-4 VP1 eluted from the column; "Post WS (post wash)" represents a sample eluted from the column in washing the column after the elution; "ELU 1-1 whole" represents the non-treated GII-4 VP1 elution fraction; "ELU 1-1 filtration" represents a sample obtained from filtrating the GII-4 VP1 elution fraction with the filter.

As shown in the FIGURE, 24 CVs of culture solution sample (AS) containing the GII-4 VP1 were collected. Further, most of the medium and the impurities from host cells were eluted in the process of post wash and could be separate from the GII-4 VP1 elution fraction. This result shows that the above method is an effective purification method of the GII-4 VLPs.

All the publications, patents, and patent applications cited in the present specification are incorporated into the present specification by reference in their entirety.

INDUSTRIAL APPLICABILITY

Since the present invention is useful as production of vaccines against norovirus, it can be utilized in an industrial field such as pharmaceutical industry.

The invention claimed is:

1. A purification method of norovirus virus-like particles, comprising: contacting solution containing norovirus virus-like particles with support for hydroxyapatite chromatography, binding the virus-like particles to the support, subsequently washing the support with buffer, and then eluting the virus-like particles from the support with buffer containing phosphate, wherein the phosphate concentration of the buffer used for elution is less than 10 mM.

2. The purification method of norovirus virus-like particles according to claim 1, wherein the phosphate concentration of the buffer used for elution is 3 to 7 mM.

3. The purification method of norovirus virus-like particles according to claim 1, wherein the buffer used for washing is buffer containing phosphate whose concentration is less than 10 mM.

4. The purification method of norovirus virus-like particles according to claim 3, wherein the phosphate concentration of the buffer used for washing is 3 to 7 mM.

5. The purification method of norovirus virus-like particles according to claim 1, wherein the solution containing norovirus virus-like particles is culture supernatant of microorganisms or cells expressing a nucleic acid sequence of norovirus.

6. The purification method of norovirus virus-like particles according to claim 1, wherein the solution containing norovirus virus-like particles is culture supernatant of insect cells expressing a nucleic acid sequence of norovirus.

7. The purification method of norovirus virus-like particles according to claim 5, wherein the nucleic acid sequence of norovirus is a nucleic acid sequence encoding norovirus structural protein VP1.

* * * * *